(12) United States Patent
Greenan

(10) Patent No.: US 10,517,748 B2
(45) Date of Patent: Dec. 31, 2019

(54) PROSTHESIS WITH GUIDE LUMEN

(71) Applicant: Medtronic Vascular, Inc., Santa Rosa, CA (US)

(72) Inventor: Trevor Greenan, Santa Rosa, CA (US)

(73) Assignee: Medtronic Vascular, Inc., Santa Rosa, CA (US)

( * ) Notice: Subject to any disclaimer, the term of this patent is extended or adjusted under 35 U.S.C. 154(b) by 179 days.

(21) Appl. No.: 15/672,105

(22) Filed: Aug. 8, 2017

(65) Prior Publication Data

US 2017/0333236 A1    Nov. 23, 2017

Related U.S. Application Data

(62) Division of application No. 11/277,976, filed on Mar. 30, 2006, now Pat. No. 9,757,260.

(51) Int. Cl.
| | | |
|---|---|---|
| *A61F 2/954* | (2013.01) | |
| *A61F 2/07* | (2013.01) | |
| *A61F 2/06* | (2013.01) | |
| *A61F 2/89* | (2013.01) | |

(52) U.S. Cl.
CPC ............... *A61F 2/954* (2013.01); *A61F 2/07* (2013.01); *A61F 2/89* (2013.01); *A61F 2002/061* (2013.01); *A61F 2002/067* (2013.01); *A61F 2002/075* (2013.01); *A61F 2230/0054* (2013.01); *A61F 2230/0078* (2013.01)

(58) Field of Classification Search
CPC .................................... A61F 2/954; A61F 2/07
See application file for complete search history.

(56) References Cited

U.S. PATENT DOCUMENTS

| | | | |
|---|---|---|---|
| 5,151,105 A | 9/1992 | Kwn-Gett | |
| 5,653,743 A * | 8/1997 | Martin | ...................... A61F 2/07 |
| | | | 606/153 |
| 5,984,955 A | 11/1999 | Wisselink | |
| 6,099,497 A | 8/2000 | Adams et al. | |
| 6,217,567 B1 | 4/2001 | Zadno-Azizi | |
| 6,264,862 B1 | 7/2001 | Wilson et al. | |
| 6,312,407 B1 | 11/2001 | Zadno-Azizi | |

(Continued)

FOREIGN PATENT DOCUMENTS

| | | |
|---|---|---|
| WO | WO03/065933 | 8/2003 |
| WO | WO04/089249 | 10/2004 |
| WO | WO06/036690 | 4/2006 |

*Primary Examiner* — Richard G Louis

(57) ABSTRACT

Tubular prosthesis for deployment in a human body passageway comprises a tubular member adapted for placement in a passageway in a human body and a tube. The tubular member has a tubular wall, first and second end openings, and a side opening formed in the tubular wall between the first and second end openings. The tube has a first end portion and a second end portion. The first end portion of the tube is disposed in the tubular member and has an opening arranged relative to the side opening such that an elongated element (e.g., a guidewire) can be passed through the tube and out from the side opening in the tubular wall where it can enter a branch passageway. The tube can be releasably secured to the tubular member in such as manner that it can be detached from the tubular member and withdrawn after the elongated element is passed through the side opening and placed in a desired position.

16 Claims, 8 Drawing Sheets

(56) References Cited

U.S. PATENT DOCUMENTS

| | | |
|---|---|---|
| 6,325,826 B1 | 12/2001 | Vardi et al. |
| 6,383,213 B2 | 5/2002 | Wilson et al. |
| 6,387,120 B2 | 5/2002 | Wilson et al. |
| 6,395,018 B1 | 5/2002 | Castaneda |
| 6,508,836 B2 | 1/2003 | Wilson et al. |
| 6,524,335 B1 | 2/2003 | Hartley et al. |
| 6,645,242 B1 | 11/2003 | Quinn |
| 6,652,567 B1 | 11/2003 | Deaton |
| 6,695,877 B2 | 2/2004 | Brucker et al. |
| 6,706,062 B2 | 3/2004 | Vardi et al. |
| 6,814,752 B1 | 11/2004 | Chuter |
| 6,858,038 B2 | 2/2005 | Heuser |
| 6,949,121 B1 | 9/2005 | Laguna |
| 7,074,235 B1 | 7/2006 | Roy |
| 7,182,771 B1 | 2/2007 | Houser et al. |
| 7,306,623 B2 | 12/2007 | Watson |
| 7,438,720 B2 | 10/2008 | Shaked |
| 7,537,606 B2 | 5/2009 | Hartley et al. |
| 7,563,270 B2 | 7/2009 | Gumm |
| 7,575,590 B2 | 8/2009 | Watson |
| 7,686,841 B2 | 3/2010 | Eidenschink et al. |
| 7,717,934 B2 | 5/2010 | Kusleika |
| 2001/0016768 A1 | 8/2001 | Wilson et al. |
| 2002/0042650 A1 | 4/2002 | Vardi et al. |
| 2002/0198585 A1* | 12/2002 | Wisselink .............. A61F 2/07 623/1.11 |
| 2003/0093145 A1 | 5/2003 | Lawrence-Brown et al. |
| 2003/0187494 A1 | 10/2003 | Loaldi |
| 2003/0199967 A1 | 10/2003 | Hartley et al. |
| 2003/0233140 A1 | 12/2003 | Hartley et al. |
| 2004/0049256 A1 | 3/2004 | Yee |
| 2004/0054404 A1 | 3/2004 | Wilson et al. |
| 2004/0093063 A1 | 5/2004 | Wright et al. |
| 2004/0106972 A1 | 6/2004 | Deaton |
| 2004/0117003 A1 | 6/2004 | Ouriel et al. |
| 2004/0167618 A1 | 8/2004 | Shaolian et al. |
| 2004/0172121 A1 | 9/2004 | Eidenschink et al. |
| 2004/0230287 A1 | 11/2004 | Hartley et al. |
| 2004/0243221 A1 | 12/2004 | Fawzi et al. |
| 2005/0131517 A1 | 6/2005 | Hartley et al. |
| 2005/0131518 A1 | 6/2005 | Hartley et al. |
| 2005/0228474 A1 | 10/2005 | Laguna |

* cited by examiner

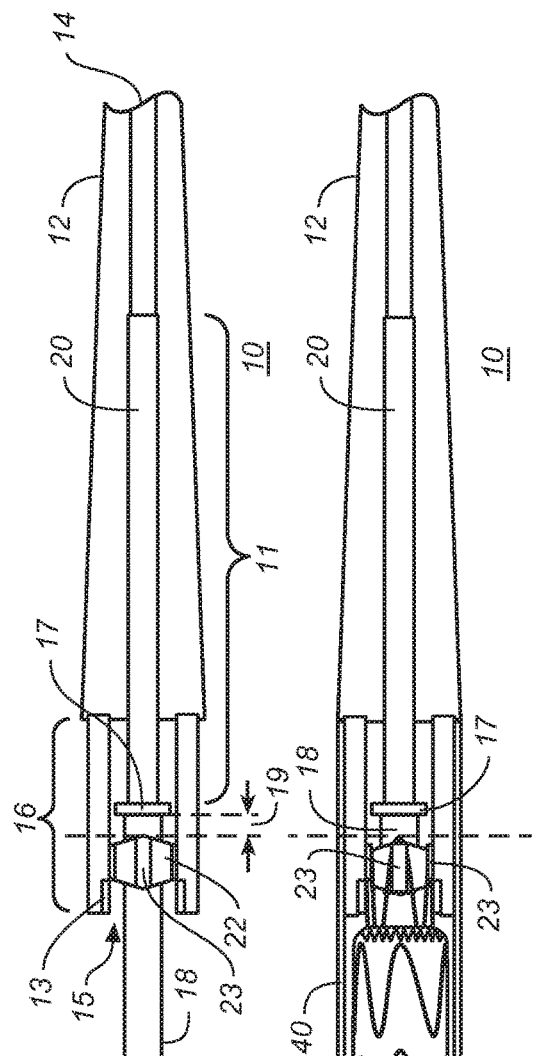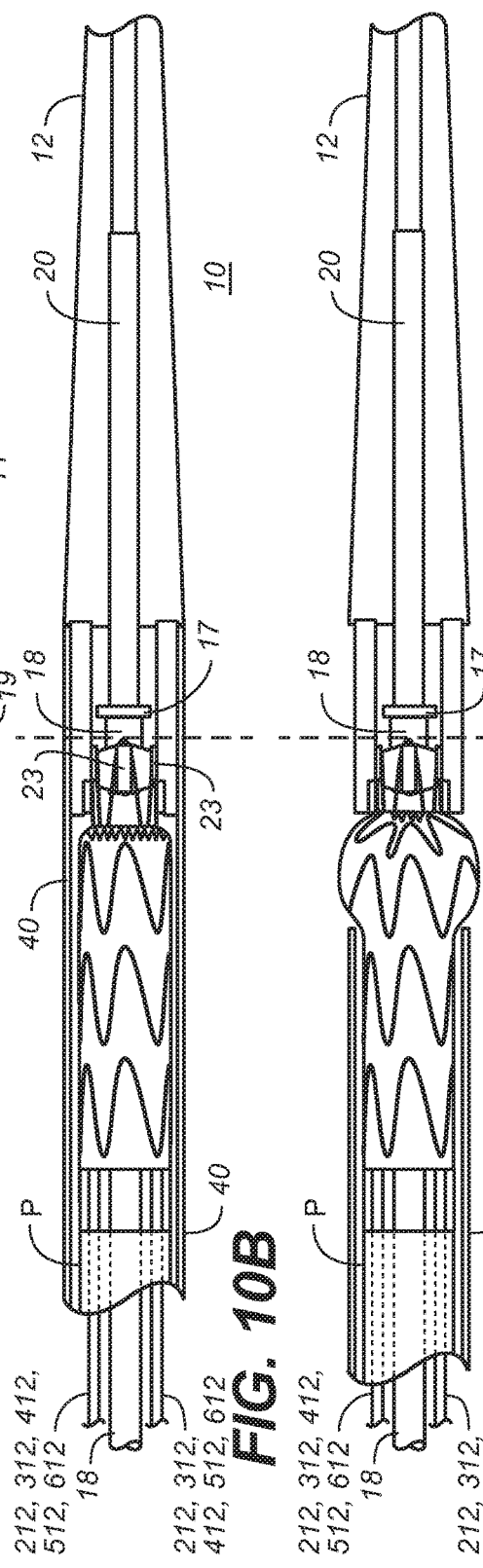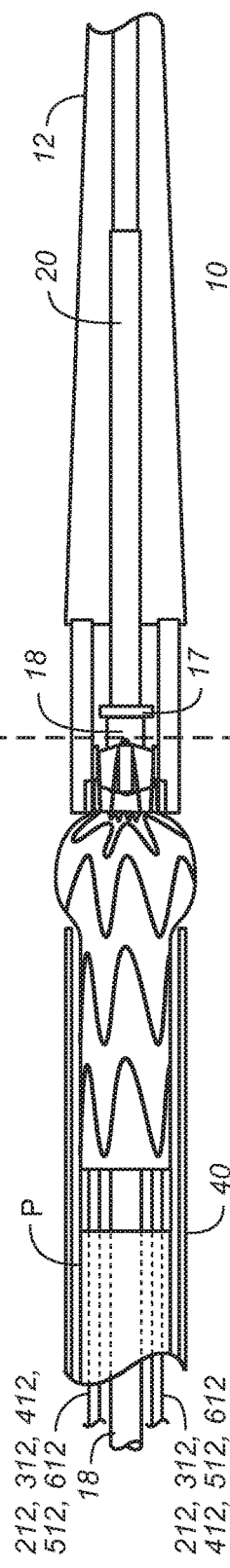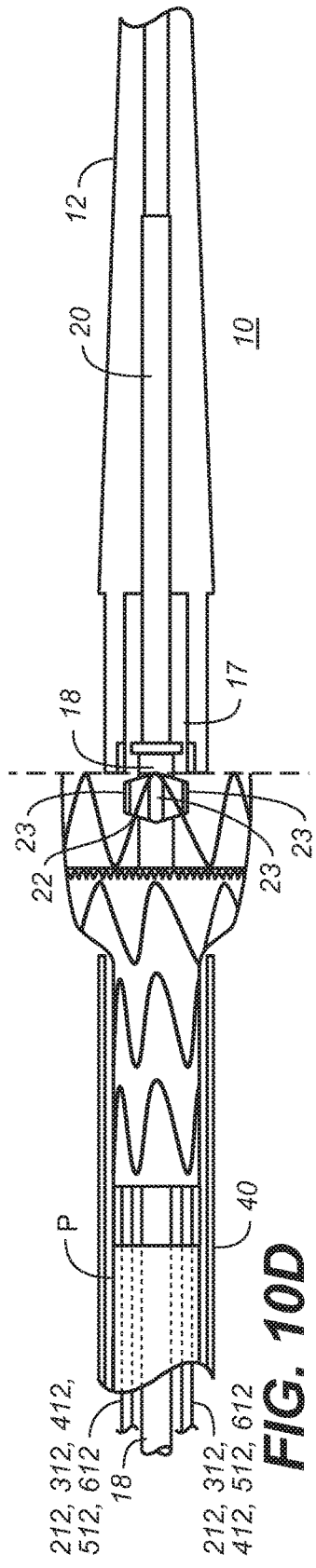

PROSTHESIS WITH GUIDE LUMEN

RELATED APPLICATIONS

This application is a Division of and claims the benefit of U.S. patent application Ser. No. 11/277,976, filed Mar. 30, 2006, now allowed. The disclosure of which is herein incorporated by reference in its entirety.

FIELD OF THE INVENTION

The invention relates to apparatus and methods for endoluminal delivery of devices such as guidewires, for example, to branch passageways in a human body.

BACKGROUND OF THE INVENTION

Tubular prostheses such as stents, grafts, and stent-grafts (e.g., stents having an inner and/or outer covering comprising graft material and which may be referred to as covered stents) have been widely used in treating abnormalities in passageways in the human body. In vascular applications, these devices often are used to replace or bypass occluded, diseased or damaged blood vessels such as stenotic or aneurysmal vessels. For example, it is well known to use stent-grafts, which comprise biocompatible graft material (e.g., Dacron® or expanded, porous polytetrafluoroethylene (ePTFE)) supported by a framework (e.g., one or more stent or stent-like structures), to treat or isolate aneurysms. The framework provides mechanical support and the graft material or liner provides a blood barrier.

Aneurysms generally involve abnormal widening of a duct or canal such as a blood vessel and generally appear in the form of a sac formed by the abnormal dilation of the duct or vessel wall. The abnormally dilated wall typically is weakened and susceptible to rupture. Aneurysms can occur in blood vessels such as in the abdominal aorta. An abdominal aortic aneurysm generally extends below the renal arteries and extends distally to or toward the iliac arteries.

In treating an aneurysm with a stent-graft, the stent-graft typically is placed so that one end of the stent-graft is situated proximally or upstream of the diseased portion of the vessel and the other end of the stent-graft is situated distally or downstream of the diseased portion of the vessel. In this manner, the stent-graft extends through the aneurysmal sac and beyond the proximal and distal ends thereof to replace or bypass the dilated wall. The graft material typically forms a blood containing lumen to facilitate endovascular exclusion of the aneurysm.

Such prostheses can be implanted in an open surgical procedure or with a minimally invasive approach. Minimally invasive endovascular stent-graft delivery generally is preferred over traditional open surgery techniques where the area of diseased vessel is surgically opened, the vessel bypassed and cut, and a prosthesis (e.g., stent-graft) sutured into position. The endovascular approach generally involves cutting through the skin to access a lumen or vasculature. Alternatively, lumenar or vascular access may be achieved percutaneously via successive dilation at a less traumatic entry point. Once access is achieved, the stent-graft can be routed through the vasculature to the target site. For example, a stent-graft delivery catheter loaded with a stent-graft can be percutaneously introduced into the vasculature (e.g., into a femoral artery) and the stent-graft delivered endovascularly to the aneurysm where it is deployed. When using an expandable stent-graft, balloon catheters generally are used to expand the stent-graft after it is positioned at the target site. When, however, a self-expanding stent-graft is used, the stent-graft generally is radially compressed or folded and placed at the distal end of a sheath or delivery catheter and allowed to expand upon deployment from the sheath or catheter at the target site. More specifically, a delivery catheter having coaxial inner and outer tubes arranged for relative axial movement therebetween can be used and loaded with a compressed self-expanding stent-graft. The stent-graft is positioned within the distal end of the outer tube (sheath) and in front of the inner tube (plunger). Once the catheter is positioned for deployment of the stent-graft at the target site, the plunger is held stationary and the outer tube withdrawn so that the stent-graft is gradually exposed and allowed to expand. An exemplary stent-graft delivery system is described in U.S. Patent Application Publication No. 2004/0093063, which published on May 13, 2004 to Wright et al. and is entitled Controlled Deployment Delivery System.

Although the endovascular approach is much less invasive, and usually requires less recovery time and involves less risk of complication as compared to open surgery, there can be concerns with management of endoluminal devices such as guidewires, especially in relatively complex applications. For example, branch vessel techniques have involved the delivery of a main device (e.g., a graft or stent-graft) and then a secondary device (e.g., a graft or stent-graft) through a fenestration or side opening in the main device and into a branch vessel.

The procedure becomes more complicated when more than one branch vessel is treated. One example is when an aortic abdominal aneurysm is to be treated and its proximal neck is diseased or damaged to the extent that it cannot support a connection and/or seal with a prosthesis. In this case, grafts or stent-grafts have been provided with fenestrations or openings formed in their side wall below a proximal portion thereof. The proximal portion is secured to the aortic wall above the renal arteries and the fenestrations or openings are aligned with the renal arteries.

To ensure alignment of the prostheses fenestrations and branch vessels, current techniques involve placing guidewires through each fenestration and branch vessel (e.g., artery) prior to releasing the main device or prosthesis. This involves manipulation of multiple wires in the aorta at the same time, while the delivery system and stent-graft are still in the aorta. In addition, an angiographic catheter, which may have been used to provide branch vessel detection and preliminary prosthesis positioning, may still be in the aorta. The foregoing approach can cause several concerns. The procedure may give rise to branch lumen guidewire entanglement with other wires and/or elements of the delivery system. There may be difficulty in accessing the fenestrations with the guidewires. Further, wires may fall out of the branch lumens and fenestrations, while the surgeon manipulates other portions of the delivery system or main device.

There remains a need to develop and/or improve delivery apparatus and approaches for endoluminal or endovascular prostheses and/or guide device placement.

SUMMARY OF THE INVENTION

The present invention involves improvements in prosthesis and/or guide device placement and overcomes disadvantages of prior art.

According to one embodiment of the invention, a tubular prosthesis for deployment in a human body passageway comprises a tubular member adapted for placement in a passageway in a human body and a tube. The tubular member has a tubular wall, first and second end opening, and a side opening formed in the tubular wall between the first and second end openings. The tube has a first end portion and a second end portion, the first end portion being disposed in the tubular member and extending toward the side opening. The tube can be releasably secured to the tubular member so that an elongated element (e.g., a guidewire) can be passed through the tube and out from the side opening in the tubular wall and the tube detached from the tubular member so that it can be moved relative to and withdrawn over the elongated element after the elongated element is placed in a desired position.

According to another embodiment of the invention, a tubular prosthesis delivery system comprises a delivery catheter having a proximal end portion and a distal end portion, a tubular prosthesis comprising a tubular wall, first and second end openings, and a side opening formed in the tubular wall between the first and second end openings. The prosthesis is positioned in the distal end portion of the delivery catheter. A tube having a first end portion and a second end portion is provided with the tube first end portion being disposed in the tubular prosthesis and having an end opening in the vicinity of the side opening and the tube second end portion extending to the proximal end portion of the delivery catheter.

According to another embodiment of the invention, a method of delivering a guide to a branch lumen comprises delivering a tubular prosthesis, which includes a side opening, an inner wall surface and a tube extending along a portion of the inner wall surface and toward the side opening, through a first passageway in a human body to a site where a second passageway branches from the first passageway; advancing a guide element through the tube and side opening and into the second passageway; and removing the tube from the tubular prosthesis.

Other features, advantages, and embodiments according to the invention will be apparent to those skilled in the art from the following description and accompanying drawings, wherein, for purposes of illustration only, specific embodiments according to the invention are set forth in detail.

BRIEF DESCRIPTION OF THE DRAWINGS

FIG. 6A illustrates endoluminally positioning the prosthesis at a target site, FIG. 6B illustrates advancing the guide devices into branch lumens or vessels, and FIG. 6C illustrates withdrawal of the prosthesis guide tubes and delivery apparatus after the guide devices have been positioned in the branch lumens and the prosthesis fully deployed.

FIG. 10A illustrates a known prosthesis restraint for releasably restraining the proximal end of a prosthesis.

FIGS. 10B-D diagrammatically illustrate a prosthesis delivery system in accordance with the invention; where FIG. 10B illustrates the prosthesis delivery system including the restraint of FIG. 10A, FIG. 10C illustrates the prosthesis of FIG. 10B partially deployed, and FIG. 10D illustrates the prosthesis of FIG. 10C with its proximal end deployed.

DETAILED DESCRIPTION

Figure 1:
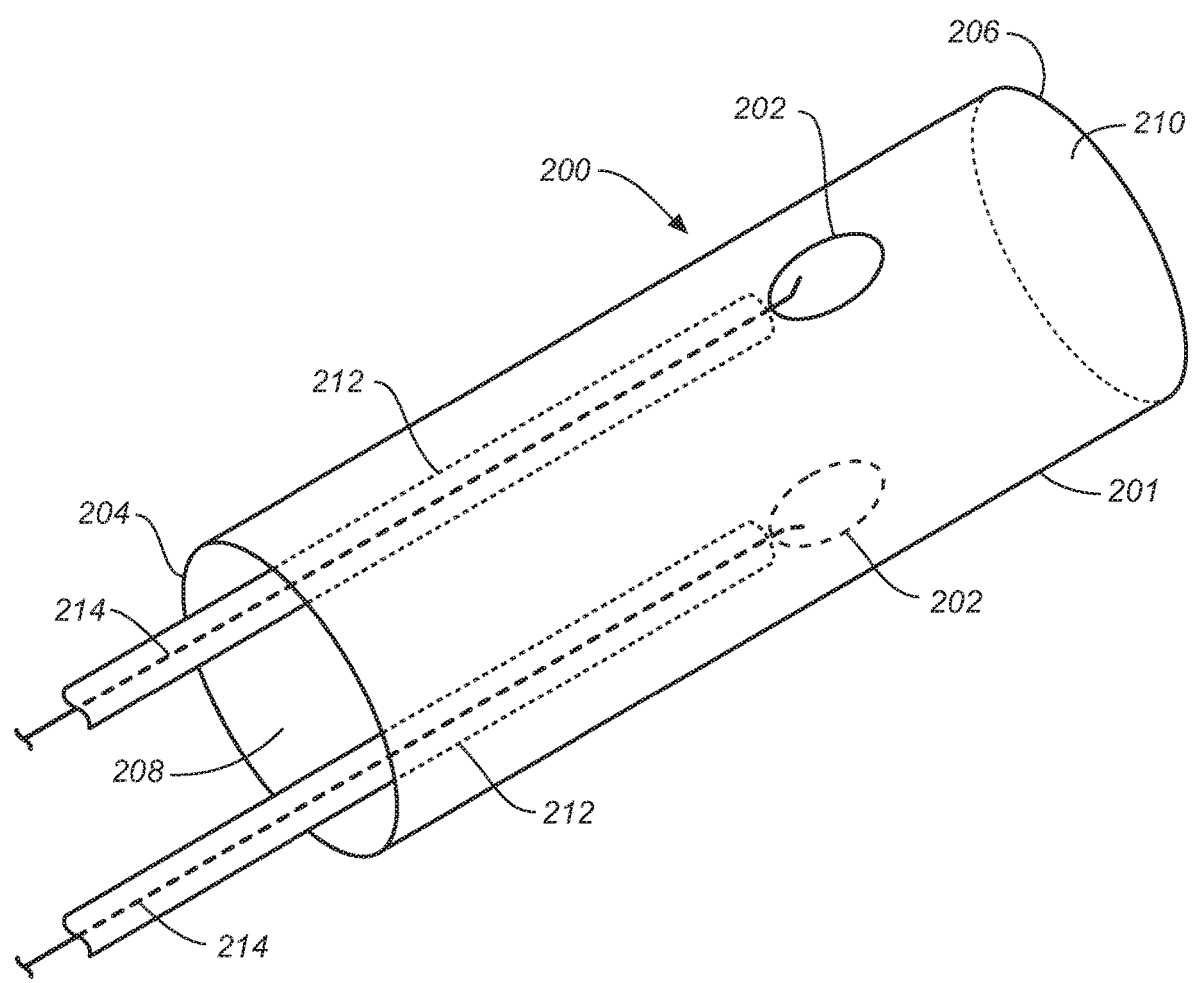
FIG. 1 is a diagrammatic view of a prosthesis having guide device lumens in accordance with one embodiment of the present invention.

The following description will be made with reference to the drawings where when referring to the various figures, it should be understood that like numerals or characters indicate like elements.

Embodiments according to the invention involve prostheses that facilitate directing and/or delivering devices from one passageway in a human body to another. In one example case, a prosthesis, which has an opening (e.g., an opening in a side wall thereof), has disposed therein a tube. The tube, which can be dedicated to guidance and/or delivery of one or more selected devices including, but not limited to guidewires, guide catheters, and/or steerable guide catheters, has an outlet that is in the vicinity of the opening. The outlet therefore can be aligned with, adjacent to or overlapping the opening. The prosthesis can be positioned in a lumen with its side wall opening in the vicinity of (e.g., aligned with, adjacent to, or overlapping) a branch lumen and a device introduced into the branch lumen from the prosthesis tube and side wall opening. For example, the prosthesis can be used to deliver a guidewire into a branch passageway for subsequent delivery of a secondary prosthesis over the guidewire so as to pass through the first passageway and into the second passageway. In such a case, the guidewire delivering prosthesis may be referred to as a main device and the secondary or branch prosthesis may be referred to as a secondary or branch device. In one variation, the tube that is disposed in the prosthesis can be releasably secured to the prosthesis so that it can be withdrawn after the guide device, which also can facilitate alignment of the side opening of the prosthesis with the branch passageway, has been delivered into the branch passageway. In another variation, the prosthesis can be provided with more than one side opening or fenestration (e.g., the prosthesis can have two side openings or fenestrations) and a tube, which can be releasably secured to the prosthesis, for each opening. In this configuration, each tube has an outlet positioned in the vicinity of a respective one of the openings so that a device such as a guidewire can be delivered through each prosthesis tube lumen and into a branch passageway. In this manner, a guidewire for guiding a catheter through a vessel and then into a branch vessel can be delivered simultaneously with the prosthesis and then delivered into the branch vessel.

The prosthesis can be in the form of a stent, graft, stent-graft or the like. Exemplary uses include, but are not limited to, the treatment of vascular diseases such as aneurysms and stenoses. For example, the tubular prosthesis is especially useful in the endovascular treatment of abdominal aortic aneurysms where the proximal neck of the aneurysm is diseased or damaged and attachment of the prosthesis to the artery above the renal arteries is desired.

According to another aspect of the invention, a delivery catheter which accommodates the prosthesis tube and the guide devices is used to place these devices at the desired location. In one embodiment where a prosthesis having two side openings is used, the delivery system is configured so that the prosthesis tubes generally extend from the prosthesis to the proximal end of the prosthesis delivery catheter or system as a one piece construction. Alternatively, the tubes can extend from the prosthesis to a member associated with the delivery catheter or system. The member would have two lumens formed therein and the lumens would extend to the proximal region of the delivery catheter or system.

In one example case, a delivery catheter comprises an axial inner and outer member arranged for relative axial movement therebetween. The outer member or sheath is tubular and the inner member has a plurality of lumens (e.g., two) formed therein and extending the length thereof. Each prosthesis tube can be coupled to or disposed in a respective inner member lumen. In the latter case, the guide tube can extend the entire length of the lumen and extend from both ends thereof. When a self-expanding tubular prosthesis is used (e.g., a self-expanding stent-graft), it is radially compressed and loaded in the outer tube or sheath at the distal end thereof and in front of the inner member, which also may be referred to as a plunger or pusher rod. Each prosthesis guide tube is placed to extend the length of a respective lumen in the inner member or plunger. Each prosthesis tube also is arranged in the inner member so that it can move or slide relative to the inner member or plunger to allow movement of the plunger or inner member without translating that motion to the prosthesis. Further, the prosthesis tubes can be constructed of material that allows them to easily collapse and have a minimal effect on the prosthesis profile so that it can be readily inserted into the sheath. One suitable material is expanded, porous polytetrafluoroethylene (ePTFE).

In the case where the Xcelerant® Delivery System manufactured by Medtronic. Inc. (Minneapolis, Minn.) is modified to accommodate the prosthesis, prosthesis tubes and guidewires, the lumens can be configured to exit from the delivery system near or at its proximal end.

Although various delivery system tube/lumen configurations have been described, it should be understood that the tubes/lumens can be associated with the delivery system in other manners.

Referring to FIG. 1, a tubular prosthesis or endoluminal device in accordance with the present invention is shown and generally designated with reference numeral 200. Prosthesis or endoluminal device 200 comprises a tubular wall 201 having openings or fenestrations 202, which can be diametrically opposed as shown in the drawing. Prosthesis 200 also has a distal end 204, proximal end 206, distal end opening 208 and proximal end opening 210. Proximal end 206 is the end that is to be oriented towards the oncoming flow of blood. In one example case, this configuration facilitates positioning the proximal end portion 203, which is the end portion above openings or fenestrations 202 (see FIG. 2A), above the renal arteries when treating an abdominal aortic aneurysm having diseased or damaged proximal neck.

Figure 2A:
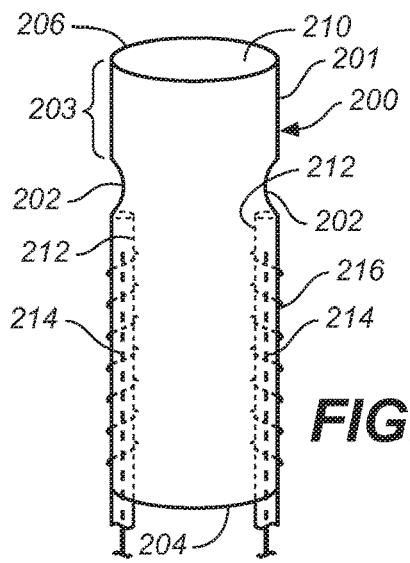
FIG. 2A is another diagrammatic view of the prosthesis of FIG. 1 showing guide devices, which can be guidewires, positioned in the prosthesis guide device tubes or lumens prior to deployment therefrom.
Figure 2B:
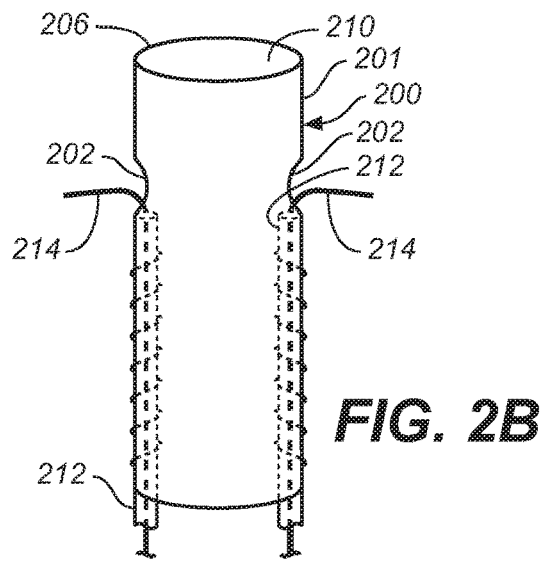
FIG. 2B depicts the prosthesis of FIG. 2A with the guide devices deployed.

Referring to FIGS. 1, 2A and 2B, prosthesis 200 further includes one or more guide tubes 212, each forming a lumen that can accommodate a guide element or device 214 in a manner such that the guide element can be reciprocated therein. That is, the guide element can be slidably arranged in a respective guide tube. Each guide tube end opening or outlet is arranged so that guide elements 214 pass through respective openings or fenestrations 202 when the guide elements are advanced from the position shown in FIG. 2A to the position shown in FIG. 2B. All guide tubes described herein can be configured and/or sized and dedicated to guidance and/or delivery of one or more selected devices including, but not limited to guidewires, guide catheters, and/or steerable guide catheters as described above. In the illustrative configuration, each guide tube is shown disposed inside the prosthesis with the guide tube outlet arranged below and adjacent to a respective side opening or fenestration. The guide tube outlets, however, can overlap the side openings or fenestrations as shown, for example, in FIGS. 3A-B and 4B-C.

Figure 3A:
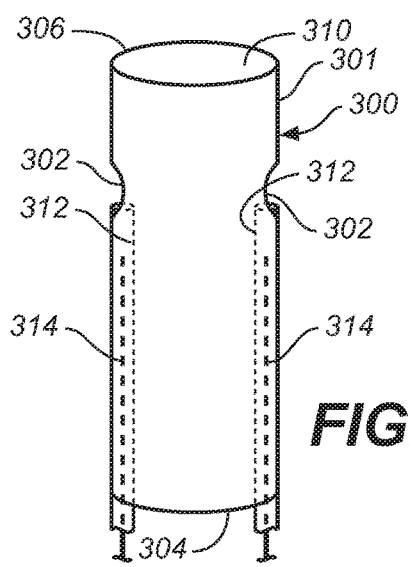
FIG. 3A is a diagrammatic view of another embodiment of the invention with guide devices positioned in prosthesis guide device lumens prior to deployment therefrom.
Figure 3B:
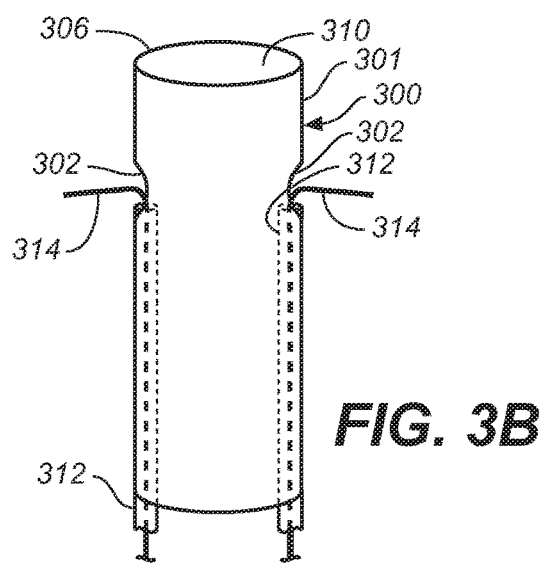
FIG. 3B depicts the embodiment of FIG. 3A with the guide devices deployed.

In FIGS. 3A-B, the guide tube outlets are shown overlapping the side opening fenestration 302. Prosthesis 300 otherwise is the same as prosthesis 200. Accordingly, prosthesis 300 includes corresponding side openings or fenestrations 302, distal end 304, proximal end 306, a distal end opening (not shown), proximal end opening 310. Guide tubes 314 similarly allow guide elements to slide therethrough and be advanced from a retracted state (FIG. 3A) to an extended or deployed state (FIG. 3B).

Guide elements 214 and 314 can be wire elements having distal end portions having shape memory set curved or bent configurations as shown in 2B or 3B. The guide elements can be formed, for example, such that the distal portions form with the adjacent portion an angle of about 60 to 120°. Any suitable shape memory material such as nitinol can be used. Methods for providing nitinol wire with a memory shape are well known in the art. For example, nitinol wire can be placed in the desired shape (e.g., that shown in FIG. 2B or 3B) and heated for about 5-15 minutes in a hot salt bath or sand having a temperature of about 480-515° C. It can then be air cooled or placed in an oil bath or water quenched depending on the desired properties.

Figure 4A:
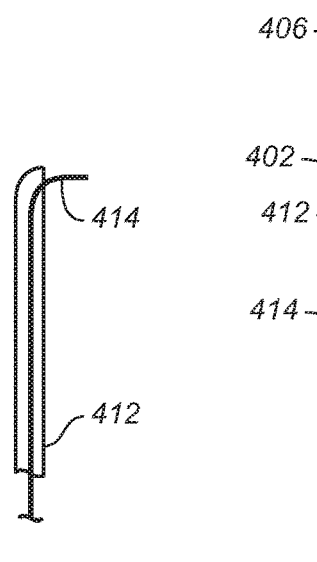
FIG. 4A illustrates a variation of a prosthesis guide tube that forms a guide device lumen in accordance with the invention.

Referring to FIG. 4A, a variation of a prosthesis guide tube is shown and designated with reference numeral 414. This guide tube has a curved end and side opening, which together assist in directing the guide element out of the prosthesis side opening and into a target branch passageway. Guide element 414 can be an elastic or superelastic wire suitable for passing through tortuous passageways that one may encounter in the human vasculature and need not have a memory shape. Guide element 414 can be a conventional guidewire. The guide element 414, however, can comprises shape memory material and have its distal end portion formed with a preset memory shape configuration such as shown in any of FIG. 4C or as described above in connection with FIGS. 2B and 3B.

Figure 4B:
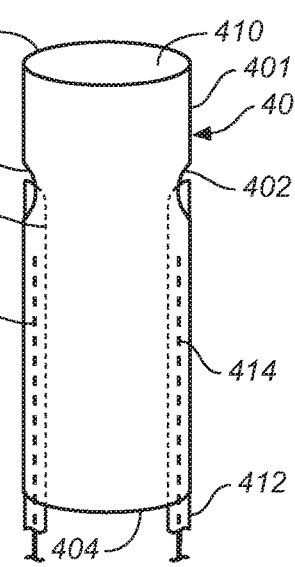
FIG. 4B diagrammatically illustrates another prosthesis in accordance with the invention with a pair of guide tubes of FIG. 4A and guide devices positioned therein prior to deployment therefrom.
Figure 4C:
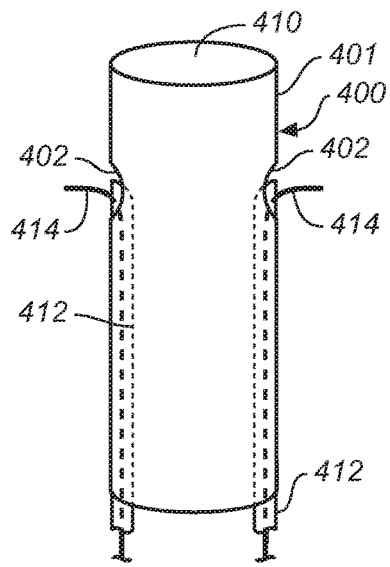
FIG. 4C depicts the prosthesis of FIG. 4B with the guide devices deployed.

Prosthesis 400 is the same as prosthesis 200 with the exception that guide tubes 414 have outlets with different configurations as described above and they overlap openings or fenestrations 402. Accordingly, prosthesis 400 includes corresponding tubular member 401, side openings or fenestrations 402, distal end 404, proximal end 406, a distal end opening (not shown), and proximal end opening 410. Guide tubes 414 similarly allow guide elements to slide therethrough and be advanced from a retracted state (FIG. 4A) to an extended or deployed state (FIG. 4B).

Each guide tube described herein can be releasably secured to the inner wall surface of the prosthesis so that the guide tube can be readily released or detached from the guide tube after deployment and the guide tube retracted as will be described in more detail below. The guide tubes can be lightly adhered to the inner wall surface of the prosthesis with biocompatible adhesive, releasably secured to the prosthesis with sutures such as sutures 216 as shown in FIG. 2A, or releasably secured to the prosthesis with other means. In the case of sutures, the sutures are wrapped around the guide tubes and sewn into the prosthesis tubular walls with a free end that can be pulled to release the guide tubes from the prosthesis. The free end can terminate near the prosthesis and be arranged for manipulation with instruments endoscopically.

Figure 5:
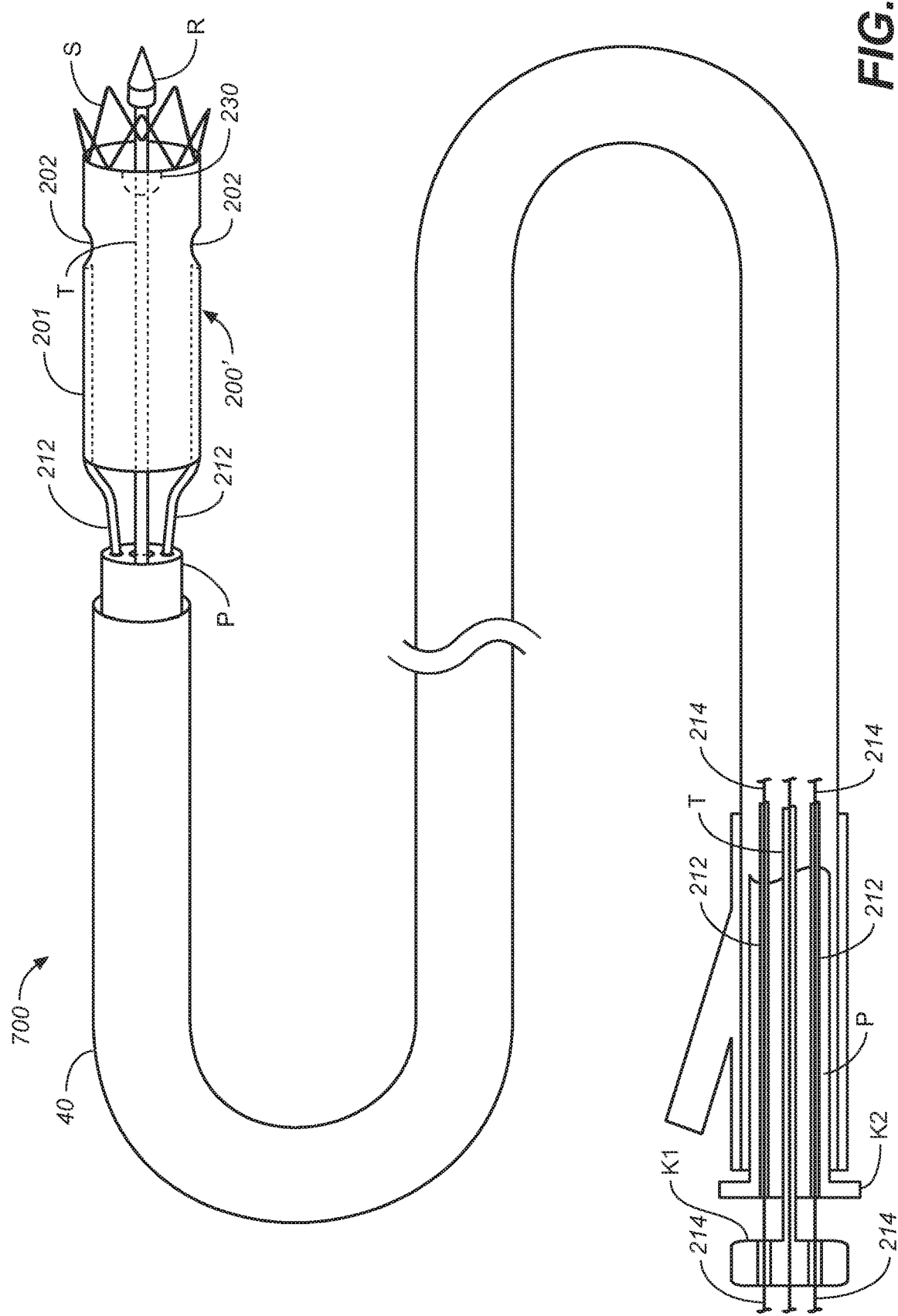
FIG. 5 diagrammatically illustrates a prosthesis delivery system with guide device lumens in accordance with the invention.

Referring to FIG. 5 an exemplary prosthesis delivery system in accordance with the invention is diagrammatically shown and generally designated with reference numeral 700. The illustrative system comprises prosthesis 200' and a prosthesis delivery catheter comprising central or inner tube T, inner member (plunger or pusher rod) P and outer member (tubular sheath) 40.

Prosthesis 200' is the same as prosthesis 200 with the exception that prosthesis 200' is shown with a proximal bare spring S secured thereto. Spring S is an annular member comprising a wire having an undulating configuration with a plurality of proximal apices. The spring has a radially outward bias so that when it is released from a radially collapsed or restrained state it expands outwardly to secure the proximal portion of the prosthesis to the target passageway wall. Any of the prosthesis described herein may include such a spring at either or both ends thereof depending on the application. It should be understood, however, that other anchoring means can be used instead of one or more end springs or in combination therewith. Prosthesis 200' also can be scalloped or provided with a cutout 230 (shown in dashed line) as can any of the prosthesis described herein when suitable for the intended application. For example, when the prosthesis is used to bypass an abdominal aortic aneurysm and its proximal portion placed above the renal arteries, cutout 230 can be provided to allow blood flow to the superior mesentery artery.

Tubular sheath 40 surrounds pusher rod P, which has formed therein along its entire length a center lumen and two diametrically opposed side lumens. Tubular sheath 40 and pusher rod P are axially movable relative to each other. Inner tube T, which may be sized to slidably receive a guidewire, is slidably disposed in the central lumen of pusher rod P, and guide tubes 212 are slidably disposed in the diametrically opposed lumens as shown. Pusher rod P and inner tube T are axially movable relative to another as are pusher rod P and prosthesis or guide tubes 212. Each tube 212 has one end portion that is releasably secured to the inner tubular surface of prosthesis tubular wall 201 and another portion that extends through the length of a respective pusher rod P lumen to the proximal end of pusher rod P (or the proximal region of the delivery system). The proximal end of tube T can be enlarged to form a knob K1 as shown in FIG. 5 to accommodate manipulation of tube T. Similarly, pusher rod P is shown with an enlarged proximal end or knob K2, which also is suitable for hand manipulation. The enlarged end portions or knobs can be integrally formed with the pusher rod and inner tube or formed as separate elements and secured or coupled to pusher rod P and inner tube T. In the illustrative embodiment, guide elements 214 pass through lumens in the proximal end or knob of pusher rod P and are slidably disposed therein to facilitate relative axial motion between the inner member (pusher rod) and guide elements and allow movement of the pusher rod without translating that motion to prosthesis 200'.

Prosthesis tubes 212 can be constructed of material so that they easily collapse and minimally affect the prosthesis profile when the prosthesis is in a collapsed state for introduction into the sheath. Suitable materials include, but are not limited to Dacron® and expanded polytetrafluoroethylene (ePTFE).

Figure 6A:
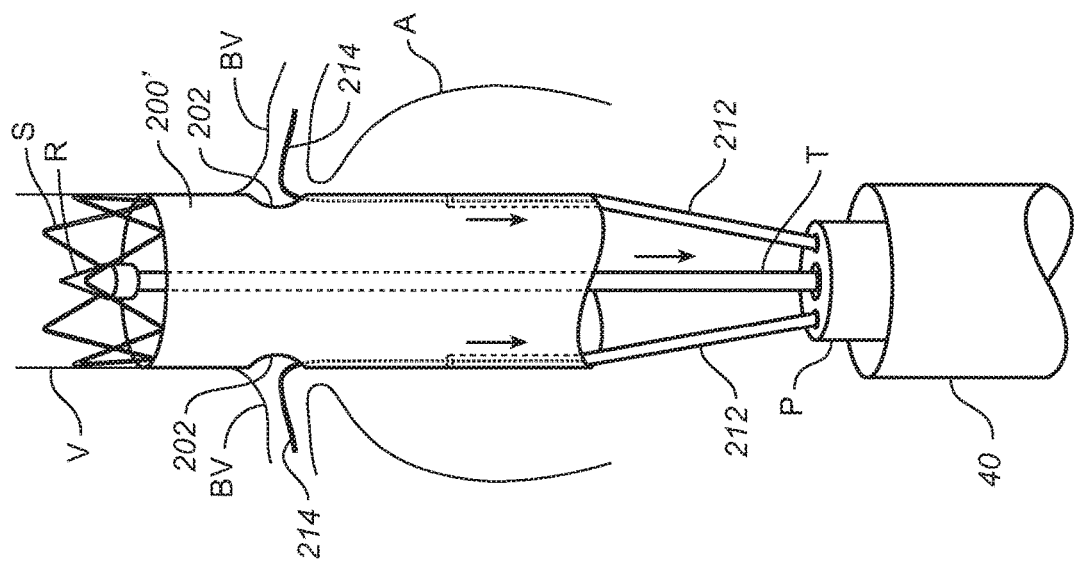
FIGS. 6A-C illustrate a method using the system of FIG. 5 in accordance with the invention; where
Figure 6B:
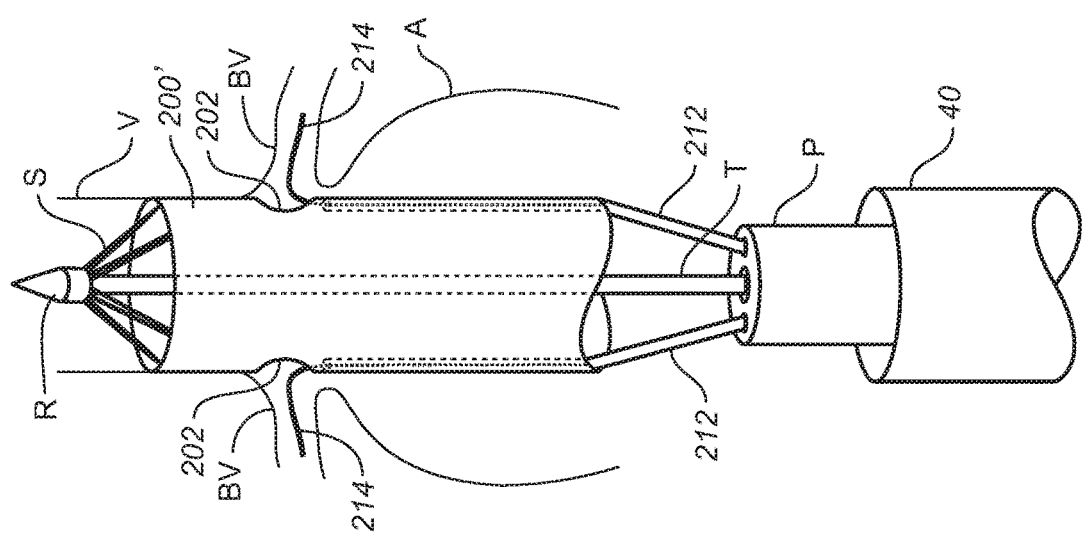
Figure 6C:
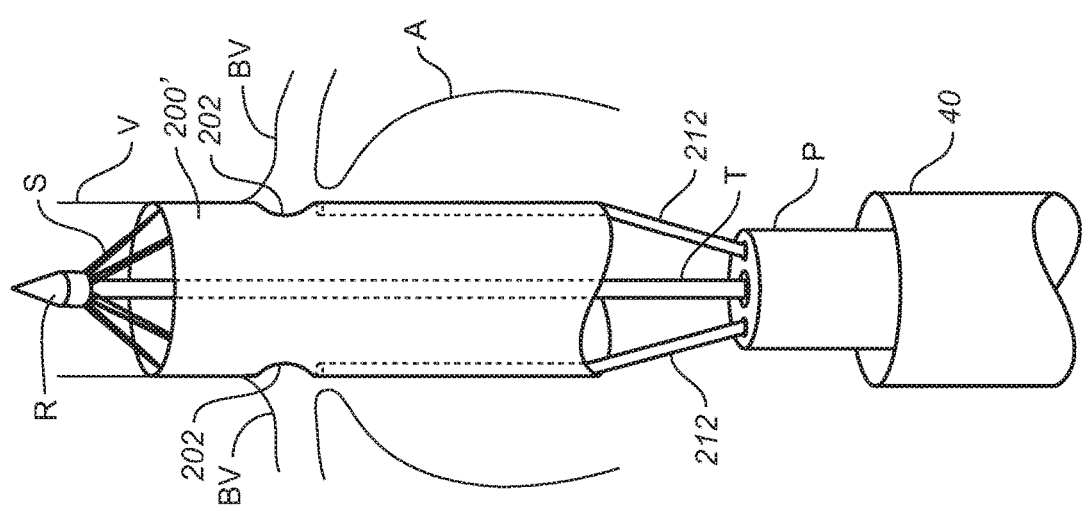

The distal end of tube T can include a restraint R coupled thereto for releasably restraining prosthesis spring S in a radially closed state as shown, for example, in FIG. 6A and allowing spring S to expand to an open state as shown in FIG. 6C.

Referring to FIGS. 6A-C, a method of the invention is set forth merely as an example. In this example, a method is described in connection with deploying the proximal end portion of prosthesis 200' upstream of branch vessels BV that are upstream of an aneurysm A. Further, in this illustrative example prosthesis 200' is a self-expanding stent graft.

Prior to introduction of the prosthesis delivery catheter with prosthesis 200' loaded therein, contrast can be injected into the target area to assist in imaging the relative positions of the branch vessels and the prosthesis as is known in the art. The prosthesis delivery catheter shown in FIG. 5 and comprising outer tube or sheath 40 and inner tube or pusher rod P can be used to endovascularly deliver the prosthesis to the target site. The catheter can be introduced into the vasculature percutaneously through, for example, one of the femoral arteries and delivered to the target site over a guidewire placed inside tube T.

Once the catheter is positioned for deployment of the prosthesis at the target site, pusher rod P is held stationary and the outer tube or sheath 40 withdrawn so that a portion of the prosthesis is gradually exposed and allowed to expand exposing the side opening or fenestration as shown in FIG. 6A. Restraint R (pictured in a schematic form, —could actually include interactive mechanism which move relative to one another to at first hold the top of the bare spring S and later by manipulations known and described in the art releases the spring S as directed by an operators manipulation of the mechanisms in the catheter—which are not shown here) restrains spring S to preclude the spring form expanding radially outward so that the stent-graft can be more easily repositioned if necessary. After prosthesis 200' has been expanded to expose the side opening fenestrations 202 and gross positioning of the prosthesis has been achieved, a first device 214 such as a first guidewire is passed through one of the tubes 212 so that the guidewire exits at or is just below a respective side opening or fenestration 214. It is then advanced to pass through fenestration 214. As it is further advanced, conformation of alignment is achieved if the wire can be successfully advanced into the branch vessel (FIG. 6B). The guidewire can be slightly retracted and the prosthesis repositioned to improve alignment without the loss of control over the wire. This procedure is repeated for the other branch vessel with the other or second guidewire 214. The containment of the first guidewire in the first tube minimizes or eliminates the risk of having the first guidewire inadvertently fall out the branch vessel while manipulating the second guidewire.

Having each guidewire contained in a dedicated lumen in the delivery system over most of its length, can minimize or eliminate the risk of entanglement with other devices. With each guide tube positioned in the vicinity of a fenestration, cannulation of the fenestration can be simplified, which can significantly reduce guidewire and catheter manipulation as compared to conventional approaches. When each guidewire is introduced through the main delivery system, the need for secondary access for either guidewire is eliminated.

The prosthesis guide tubes can be configured and/or sized to accommodate guide catheters, which can be steerable guide catheters. The guide catheter can assist with navigation of the guidewire between the fenestration and branch vessel. Similar advantages to those described above may be achieved.

Referring to FIG. 6C, the delivery system is removed after guidewire access has been achieved for all branches and the guidewires left in place. Prior to or during the withdrawal of the delivery system, tubes 212 are detached from the prosthesis. In the case where each tube is lightly adhered to the inner wall of the prosthesis, the pusher rod can be slowly retracted (the prosthesis being fully expanded and secured in place) as shown in FIG. 6C to remove tubes 212 without displacing stent-graft 200'. Where tubes 212 are attached with a wire or suture, the wire or suture can be manipulated independently to release tubes 212 from the prosthesis. The guidewires most likely may need to be pushed forward slightly during removal of the system to prevent retracting the guidewires as well. This type of guidewire manipulation is common practice when exchanging devices over guidewires. Balloons can be added to the guidewires in a manner similar to PercuSurge Guardwire Plus type devices, e.g., see U.S. Pat. Nos. 6,312,407 and 6,217,567, to anchor them in position during delivery catheter removal.

Figure 7:
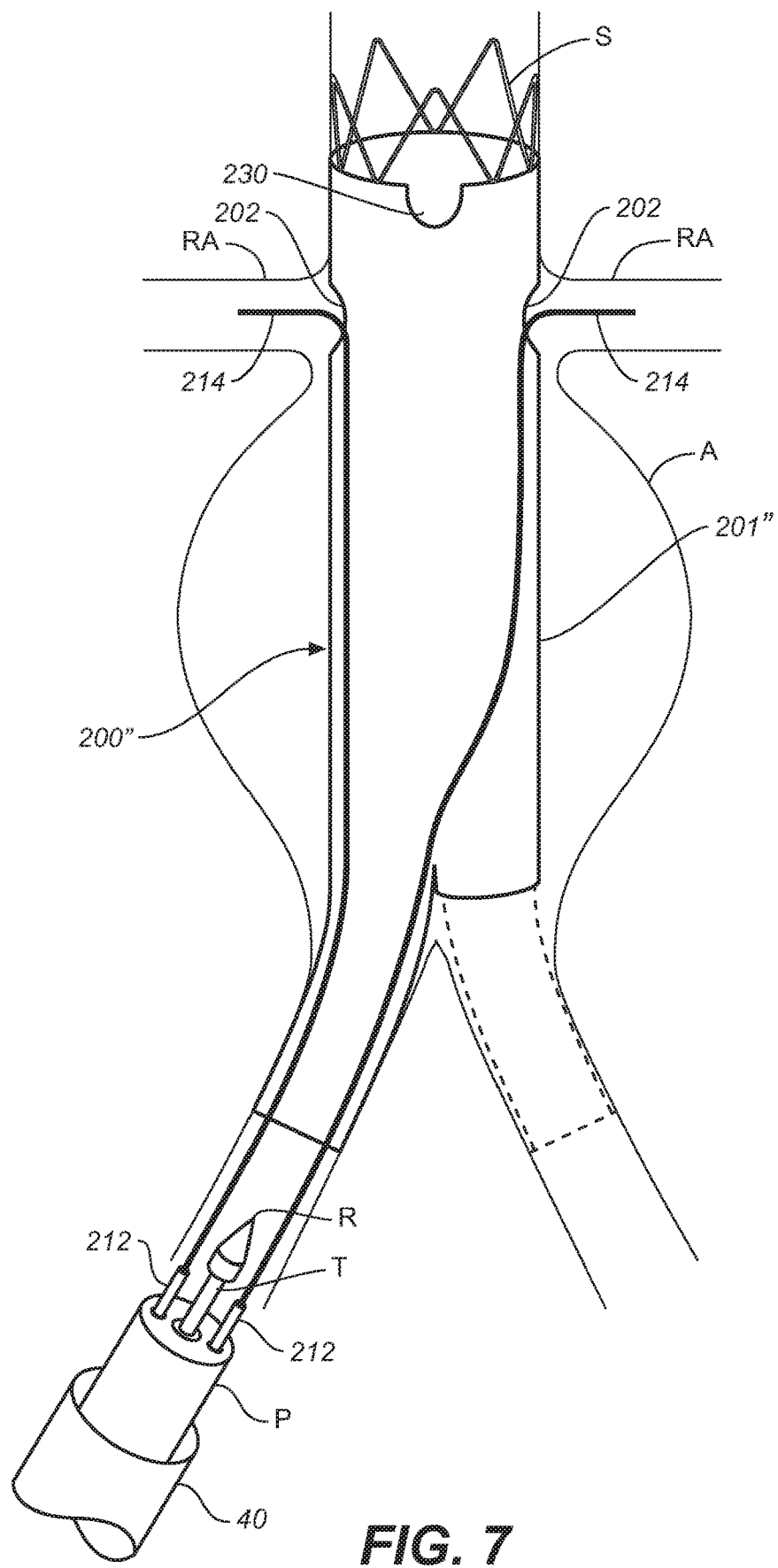
FIG. 7 illustrates a bifurcated embodiment of a prosthesis in accordance with the invention showing withdrawal of the prosthesis guide tubes and delivery apparatus after the guide devices have been positioned in the branch lumens and the prosthesis fully deployed.

FIG. 7 diagrammatically illustrates a bifurcated tubular prosthesis 200", which can be in the form of a stent-graft, positioned to bypass aneurysm A, which in this example is an abdominal aortic aneurysm. Prosthesis 200" is similar to prosthesis 200', but comprises tubular wall 201", which has a bifurcated configuration. In use, openings or fenestrations 202 are aligned with renal arteries RA with the ipsilateral leg of the prosthesis extending into one of the iliac arteries. The guidewires then are advanced into the renal arteries, guide tubes 212 detached from the prosthesis and the delivery catheter (including sheath 40, pusher rod P and tube T) and the guide tubes withdrawn. The contralateral leg of the prosthesis is shown in dashed line and can be delivered endovascularly through the other femoral and iliac artery and coupled to the main body of prosthesis 200" in accordance with conventional techniques. The proximal end of prosthesis 200" also can be scalloped or provided with a cutout 230 to allow blood flow to the superior mesentery artery as described above.

Figure 8:
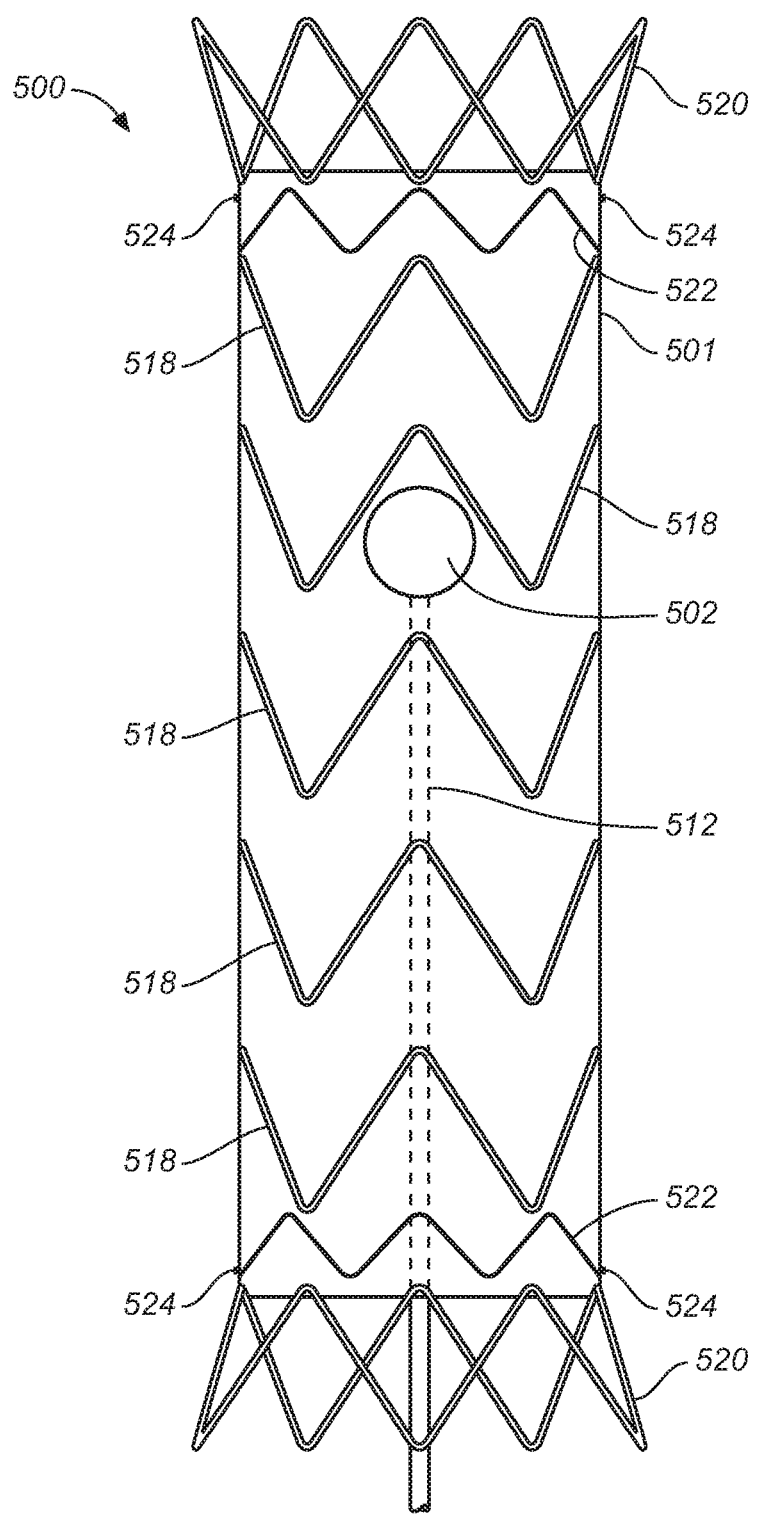
FIG. 8 is a front elevational view of a stent-graft in accordance with the invention.

Referring to FIG. 8, another prosthesis in accordance with the invention is shown and generally designated with reference numeral 500. Prosthesis 500 is a stent-graft having a tubular portion 501 comprising any suitable graft material, annular undulating wire spring elements or stents 518 which structurally support tubular graft 501 and are secured thereto using conventional techniques. Tubular graft portion 501 can be positioned on the interior and/or exterior of the wire spring elements 518. Undulating wire support springs 522 can be provided at both ends of tubular graft 501 to provide radial strength and also can be positioned on the interior and/or exterior thereof. Bare springs 520, which can correspond to spring S described above, also have an undulating configuration and have a radially outward biased configuration when a free state (e.g., a released state). In this manner, they serve to secure the graft against the wall forming a lumen in which the prosthesis is to be placed. Springs 520 can be attached to either or both ends of tubular graft 501 depending on the desired anchoring at the target site. It should be understood, however, that other anchoring means can be used in lieu of springs 510 or in combination with either or both springs 520. The spring elements or stents, support springs, and bare springs can be of any suitable material as would be apparent to one of ordinary skill in the art. One suitable material is nitinol. The graft material also can be any suitable material such as Dacron® or expanded polytetrafluoroethylene (ePTFE).

Tubular member 501 includes one or more openings or fenestrations 502, which can be the same as openings or fenestration 202, 302 or 402, and a guide tube 512 associated with each opening or fenestration in the same manner as described above in connection with guide tubes 212, 312, or 412. Radiopaque markers 524 also can be provided to facilitate positioning openings or fenestrations 502 adjacent to the branch vessel opening(s). Such markers can be secured to the prosthesis with any suitable methods, i.e., sutures.

Figure 9:
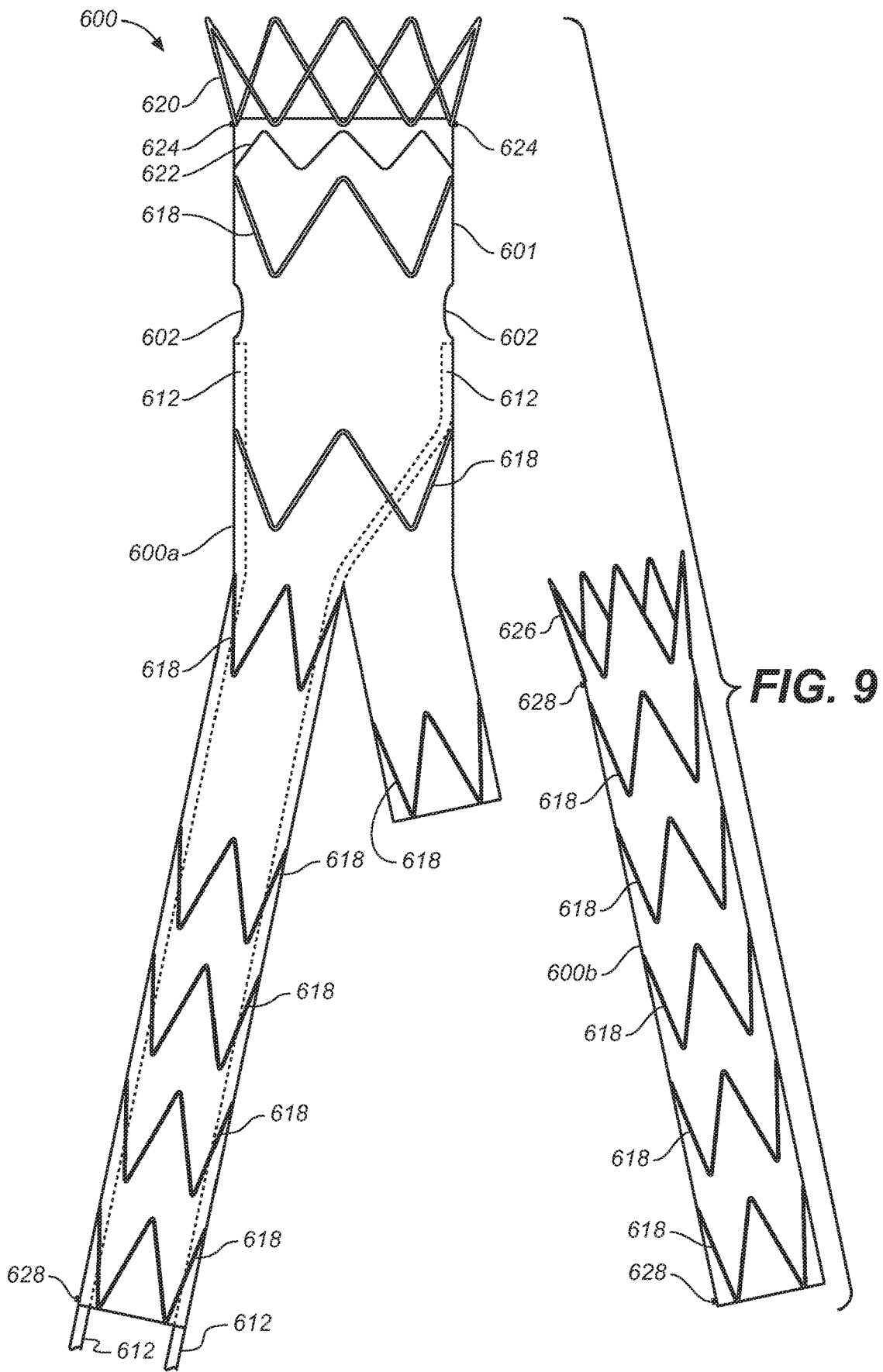
FIG. 9 is a front elevational view of a bifurcated stent-graft in accordance with the invention.

Referring to FIG. 9, another prosthesis in accordance with the invention and generally designated with reference numeral 600 is shown. Prosthesis 600 is a bifurcated stent-graft having a modular construction, which includes portions 600a (having and ipsilateral leg portion) and 600b (the contralateral leg portion) to facilitate delivery and deployment at a bifurcated passageway such as where the aorta branches to the iliac arteries. The contralateral leg portion 600b can be coupled to main portion 600a in situ as is as is known in the art. Stent-graft portion 600a comprises a bifurcated tubular member 601 comprising any suitable graft material as described above and annular undulating wire spring elements or stents 618, which structurally support bifurcated tubular graft 601 as is conventional in the art. Tubular graft portion 601 can be positioned on the interior and/or exterior of the wire spring elements 618. Undulating wire support spring 622 can be provided at the proximal end of prosthesis 600 and another (not shown) can be provided along the ipsilateral leg portion of tubular graft 601 to provide radial strength and also can be positioned on the interior and/or exterior thereof. Bare spring 620 can be the same as bare spring 520 with the same radial outward biased configuration. A similar spring can be placed at the distal end of the ipsilateral leg portion of tubular graft 601 in combination with the proximal spring or alone depending on the desired fixation. It should be understood, however, that other anchoring means can be used in lieu of springs 620 or in combination with either or both springs 620. The spring elements or stents, support springs, and bare springs can be of any suitable material as would be apparent to one of ordinary skill in the art. One suitable material is nitinol. The graft material also can be any suitable material such as Dacron® or expanded polytetrafluoroethylene (ePTFE).

Tubular member 601 includes one or more openings or fenestrations 602, which can be the same as openings or fenestration 202, 302, 402, or 502 and a guide tube 612 associated with each opening or fenestration in the same manner as described above in connection with guide tubes 212, 312, 412, or 512.

Contralateral leg portion 600b comprises a tubular graft member and annular wire springs or stents 618, which can be secured to the graft member in the same manner as springs 618 are coupled to bifurcated tubular graft member 601. Further, graft material can extend into the apices of the proximal spring 626 of the contralateral leg as shown in FIG. 9. Proximal spring 626 can be biased radially outward to enhance the connection to the contralateral portion of bifurcated tubular member 601 when inserted therein.

Radiopaque markers 624 or 628 also can be provided to facilitate positioning the stent-graft portions at the desired location.

Restraint R can be in different forms. FIGS. 10A-D show portions of a delivery system 10 in accordance with the invention using a proximal spring restraint described in U.S. Patent Application Publication No. 2004/0093063A1, the entire disclosure of said application publication being hereby incorporated by reference herein. The vertical dashed line provides a reference line to provide correlation between the figures to a common location related to the position of the end spring of the prosthesis (which in the illustrative embodiment is a stent-graft) as elements of the delivery system are manipulated to first partially deploy and then fully deploy the proximal end of the stent-graft, which may be any of the stent-grafts described herein.

FIG. 10A illustrates the distal tapered tip portion (which is disclosed U.S. Patent Application Publication No. 2004/0093063A1) of the delivery system 10 alone and without a stent-graft, while FIGS. 10B-D show close up views of the tip portion loaded with a stent-graft constructed in accordance with the present invention, with progressive figures showing deployment from within a retractable primary sheath 40.

A configuration of the stent-graft deployment system 10 includes a tapered tip 12 that is flexible and able to provide trackability in tight and tortuous vessels. The tapered tip 12 can include a lumen 14 allowing for passage of a guidewire, for example. Other tip shapes such as bullet-shaped tips could also be used.

The retractable primary sheath 40 (which can be made of semi-rigid material such as PTFE) in an unretracted position contains the stent-graft in a first constrained diameter configuration as shown in FIG. 10B. An outer tube 18, which can correspond to tube T described above, is located within the retractable primary sheath 40 and within the stent-graft as shown in FIGS. 10B-D. An inner tube 20 within the outer tube 18 serves as a guidewire lumen. The inner tube 20 and the outer tube 18 can move along the longitudinal axis relative to each other and can also move along the longitudinal axis relative to the retractable primary sheath. A cap 15 is coupled to a distal area or end portion 11 of the inner tube 20 and is further configured to retain at least a portion of a proximal end of the stent-graft in a radially compressed configuration. Actuating members at the operator's end of the catheter create a relative force in the axial direction to provide a controlled relative axial movement between the outer tube 18 and the inner tube 20 to precisely control the release of the proximal end of the stent-graft (such as proximal springs) from the cap and from the radially compressed configuration.

Referring to FIG. 10B, the stent-graft is located within the retractable primary sheath 40 in a pre-deployment unretracted position.

FIG. 10C illustrates system 10 with sheath 40 partially retracted. The proximal end (tip) of the stent-graft is constrained while a proximal portion of the stent-graft (that is now exposed due to the partial retraction of sheath 40) between the end of the sheath 40 and the constrained proximal end (tip) is partially deployed, which allows longitudinal repositioning of the stent-graft before releasing the proximal end (the release of the proximal end of the stent-graft prevents repositioning of the stent-graft in a direction toward the proximal end of the stent-graft, while depending on the degree of expansion and contact between the stent-graft and the wall of the vessel in which the stent-graft is being deployed, some pull down (movement toward the distal end of the stent-graft) of the stent-graft is possible. Deployment of the stent-graft can be halted and the stent-graft repositioned, rotated or moved in either direction axially.

In FIG. 10D, the proximal end of the stent-graft is shown as having been deployed by the controlled relative axial movement between the inner tube 20 and the outer tube 18. In particular, as shown in FIGS. 10B-D, an end cap 15 containing the proximal apices of the end spring to the stent-graft can be formed from a shroud portion of the tapered tip 12, which is coupled to the distal end of the outer tube 18. Within the shroud portion (formed by tubular body portion 16 of the tapered tip 12) can reside a back plate 17 coupled to a distal portion or end of outer tube 18 that serves as a proximal stop for the stent-graft. The tubular body portion 16 of the shroud portion may also include a support (reinforcing) ring 13 near the proximal end of the tapered tip 12 to provide additional rigidity to the cap and minimize or eliminate the risk of the cap shroud portion 16, which can be made of plastic material, from stretching (or distorting) in diameter. This configuration can thereby prevent premature release of the proximal end of the stent-graft constrained by the cap (premature stretching could create a gap large enough for the restrained members of the stent-graft to spring loose. Additionally, a proximal lock (retainer 22 is also coupled to a distal portion of the outer tube 18. The proximal lock 22 can include at least one or a plurality of ribs (or splines) 23 that can together with the shroud portion 16 serve as an axial constraint for the end of the stent-graft. The proximal end (or the proximal spring) of the stent-graft cannot deploy until the proximal end of the ribs of the proximal lock clear the end of the shroud portion 16 of the tip.

As shown, the gap 19 between the backplate 17 and the proximal lock 22, can be designed to hold the protruding apices of the proximal spring. The apices straddle the ribs 23 of the proximal lock 22 and remain trapped between the back plate and the proximal lock until relative movement between the outer tube 18 and the inner tube 20 exposes the gap 19 and releases the apices of the proximal spring as shown in FIG. 10D. In other words, the apices cannot release from the ribs 23 on the proximal lock 22 while the apices remain within the shroud portion 15. When the inner tube 20 and tapered tip 12 assembly are advanced forward exposing the proximal lock 22, the apices of the proximal spring release from the respective ribs 23 of the proximal lock 22. The release results in the deployment of the proximal end of the stent-graft as shown in FIG. 10D. Note that while the apices of the proximal spring remain in gap 19 and within the cap or shroud portion of the tapered tip 12, the whole of the proximal spring remains axially (longitudinally) constrained as well as radially constrained. The support ring 12, usually made of metal, helps prevent the radial force of the proximal springs from distorting the shape of the tapered tip and particularly the shroud portion of the tapered tip.

Although one particular restraint R has been shown, it should be understood that other configurations can be used. For example, other proximal tip deployment systems also described in U.S. Patent Application Publication No. 2004/0093063A1 can be used as well. The disclosure of U.S.

Patent Application Publication No. 2004/0093063A1 is incorporated herein in its entirety.

Any feature described in any one embodiment described herein can be combined with any other feature of any of the other embodiments.

Variations and modifications of the devices and methods disclosed herein will be readily apparent to persons skilled in the art.

What is claimed is:

1. A tubular prosthesis delivery system comprising a delivery catheter having a proximal end portion and a distal end portion, a tubular prosthesis comprising a tubular wall, first and second end openings, and a side opening formed in said tubular wall between said first and second end openings, said prosthesis being positioned in said distal end portion of said delivery catheter, and a tube having a first end portion and a second end portion, said tube first end portion being disposed in said tubular prosthesis and having an end opening in the vicinity of said side opening and said tube second end portion extending to said proximal end portion of said delivery catheter, wherein said delivery catheter comprises a sheath and a pusher rod slidably disposed therein, said pusher rod having a lumen formed therein and extending in an axial direction thereof, and said tube extending through said pusher rod lumen.

2. The delivery system of claim 1, wherein said pusher rod comprises an end portion facing said tubular prosthesis.

3. The delivery system of claim 2, wherein said tube is releasably secured to said tubular prosthesis.

4. The delivery system of claim 3 wherein said tube is releasably secured to said tubular prosthesis with adhesive.

5. The delivery system of claim 3 wherein said tube is releasably secured to said tubular prosthesis with a suture.

6. The delivery system of claim 3 wherein said tube is releasably secured to said tubular prosthesis with a wire.

7. The delivery system of claim 3 wherein said sheath and said pusher rod are axially movable relative to each other.

8. The delivery system of claim 1, wherein said tube is releasably secured to said tubular prosthesis.

9. The delivery system of claim 1, wherein a guidewire extends through at least a portion of said lumen and said tube.

10. The delivery system of claim 1, wherein said prosthesis has a radially collapsed state and a radially expanded state, said tubular prosthesis being in said collapsed state.

11. The delivery system of claim 1, further including a second side opening formed in said prosthesis between said first and second end openings and a second tube having a first end portion and a second end portion, said second tube first end portion being disposed in said prosthesis and extending toward said second side opening.

12. The delivery system of claim 11 wherein said second tube is releasably secured to said prosthesis.

13. The delivery system of claim 11 wherein a second guidewire can be passed through said second tube and out from said second side opening in said prosthesis.

14. The delivery system of claim 11 wherein said pusher rod further comprises a second lumen, said second tube extending through said pusher rod second lumen.

15. The delivery system of claim 1 wherein said pusher rod comprises a central lumen, the delivery system further comprising an inner tube slidably disposed in said pusher rod central lumen.

16. The delivery system of claim 15 wherein said inner tube is configured to receive a guidewire therein.

* * * * *